United States Patent
Dindi et al.

(10) Patent No.: US 6,825,389 B2
(45) Date of Patent: Nov. 30, 2004

(54) PROCESS FOR MANUFACTURING DIIODOPERFLUOROALKANES

(75) Inventors: Hasan Dindi, Wilmington, DE (US); John Joseph Hagedorn, Newark, DE (US); Ming-Hong Hung, Wilmington, DE (US)

(73) Assignee: DuPont Dow Elastomers LLC, Wilmington, DE (US)

( * ) Notice: Subject to any disclaimer, the term of this patent is extended or adjusted under 35 U.S.C. 154(b) by 108 days.

(21) Appl. No.: 10/301,181

(22) Filed: Nov. 21, 2002

(65) Prior Publication Data

US 2004/0102665 A1 May 27, 2004

(51) Int. Cl.$^7$ .............................................. C07C 17/00
(52) U.S. Cl. ...................................................... 570/139
(58) Field of Search ......................................... 570/139

(56) References Cited

U.S. PATENT DOCUMENTS

| | | | | |
|---|---|---|---|---|
| 3,016,407 A | * | 1/1962 | Brace | 570/125 |
| 4,833,274 A | * | 5/1989 | Caporiccio et al. | 570/137 |
| 5,214,106 A | | 5/1993 | Carlson et al. | |

FOREIGN PATENT DOCUMENTS

| | | |
|---|---|---|
| GB | 1218528 A | 1/1971 |
| GB | 1301617 A | 1/1973 |
| JP | 6131084 | 7/1986 |

OTHER PUBLICATIONS

Clifford D. Bedford and Kurt Baum, Preparation of a,w–Diiodoperfluoroalkanes, J. Org Chem., 1980, 347–348, 45.

Tortelli, V., et al., "Telomerization of tetrafluoroethylene and hexafluoropropene: synthesis of diiodoperfluoroelkanes", Journal of Organic Chemistry (1980), 347–8, 45(2).

Atkinson B., et al., "The thermal decomposition of tetrafluoroethylene", Journal of the Chemical Society, Chemical Society, 1957, pp. 2086–2094, Letchworth, Great Britain.

* cited by examiner

Primary Examiner—Michael L. Shippen

(57) ABSTRACT

The present invention involves a process for the manufacture of α, ω-diiodoperfluoroalkanes of the formula I—$(CF_2CF_2)_n$—I, wherein n is an integer between 2 and 6. The latter compounds are produced at relatively high conversions and under relatively mild reaction temperatures and pressures, compared to prior art processes, by the elimination of the gaseous byproduct perfluorocyclobutane throughout the process.

8 Claims, No Drawings

PROCESS FOR MANUFACTURING DIIODOPERFLUOROALKANES

FIELD OF THE INVENTION

This invention relates to a process for the manufacture of α, ω-diiodoperfluoroalkanes from the reaction of tetrafluoroethylene and 1,2-diiodoperfluoroethane with periodic removal of the byproduct perfluorocyclobutane.

BACKGROUND OF THE INVENTION

It is known that α, ω-diiodoperfluoroalkanes, represented by the formula I—$(CF_2CF_2)_n$—I, where n is an integer between 2 and 6, are useful as reagents in the synthesis of various fluorochemicals and fluoropolymers. For example, Carlson et al. (U.S. Pat. No. 5,214,106) disclose fluoroelastomers having terminal iodo groups formed by polymerization in the presence of one or more of these α, ω-diiodoperfluoroalkanes.

In general, the manufacture of α, ω-diiodoperfluoroalkanes from iodine and tetrafluoroethylene (TFE), or from 1,2-diiodoperfluoroethane and TFE requires a high reaction temperature (>240° C.) and a high TFE pressure (>3.1 MPa) for reasonable conversion and yield (i.e. for less than 40 mole % of unreacted 1,2-diiodoperfluoroethane remaining in the product mixture).

Bedford and Baum (J. Org. Chem. 1980, 45, 347–348) disclose a laboratory-scale method for preparing α, ω-diiodoperfluoroalkanes by the telomerization of iodine and tetrafluoroethylene. However, the yield and conversion were quite poor.

Suzuki et al. (JP 61-31084) disclose the manufacture of 1,4-diiodoperfluorobutane (and higher order diiodoperfluoroalkanes) by the thermal decomposition of 1,2-diiodoperfluoroethane with the pre-addition of iodine and an inert gas to the reactor. However, conversion is still rather low and the resulting product must be separated from a large amount of iodine.

It is an object of the present invention to manufacture α, ω-diiodoperfluoroalkanes under relatively mild conditions in a process having relatively high conversions and wherein minimal amounts of iodine must be separated from the diiodoperfluoroalkanes produced.

SUMMARY OF THE INVENTION

Applicants have developed a relatively low temperature and low pressure process, having acceptable conversions, for the manufacture of diiodoperfluoroalkanes. Accordingly, an aspect of the instant invention is a process for preparing α, ω-diiodoperfluoroalkanes comprising the steps of:

A. heating 1,2-diiodoperfluoroethane in a reactor to a temperature between 200° and 240° C.;

B. adding to said reactor a quantity of tetrafluoroethylene so as to result in a total pressure in said reactor of between 1.7 and 3.4 MPa;

C. maintaining said temperature and pressure for a period of time to form a mixture of α, ω-diiodoperfluoroalkanes and perfluorocyclobutane;

D. cooling said mixture to a temperature below 75° C. and then discharging gaseous perfluorocyclobutane and unreacted tetrafluoroethylene from said reactor, leaving a liquid mixture in said reactor;

E. heating said liquid mixture to a temperature between 160° and 235° C.; and

F. repeating steps B)–E) until a desired mixture has been prepared of α, ω-diiodoperfluoroalkanes of the formula I—$(CF_2CF_2)_n$—I, wherein n is an integer from 2 to 6.

DETAILED DESCRIPTION OF THE INVENTION

The present invention is a process for manufacturing α, ω-diiodoperfluoroalkanes from 1,2-diiodoperfluoroethane and tetrafluoroethylene (TFE). The α, ω-diiodoperfluoroalkanes made by this process are of the formula I—$(CF_2CF_2)_n$—I, wherein n is an integer from 2 to 6.

In the process of the present invention, 1,2-diiodoperfluoroethane is first heated in a reactor to a temperature sufficient for it to thermally decompose to the I—$(CF_2CF_2)$·radical. This temperature is typically in the range of 200° to 240° C., preferably 210° to 235° C. and most preferably 220° to 230° C.

A molar excess quantity of tetrafluoroethylene is then fed to the reactor so that the total reactor pressure is in the range of 1.7 to 3.4 MPa (preferably 2.1 to 3.1 MPa, most preferably 2.6 to 2.9 MPa). The temperature and pressure is maintained in this range for a period of time, typically 5 to 20 hours to allow the telomerization reaction to take place, forming α, ω-diiodoperfluoroalkanes.

During this reaction period, a competing reaction forms the byproduct perfluorocyclobutane via dimerization of TFE. The perfluorocyclobutane inhibits the formation of the α, ω-diiodoperfluoroalkanes. Applicants have found that removal of the perfluorocyclobutane (i.e. TFE-dimer) from the reactor throughout the reaction period, greatly improves the conversion of 1,2-diiodoperfluoroethane. Thus, at least once (preferably at least twice, most preferably at least three times) during the reaction period, the mixture in the reactor is cooled to a temperature below 75° C. so that the unreacted 1,2-diiodoperfluoroethane and α, ω-diiodoperfluoroalkanes are in the liquid state. Unreacted TFE and gaseous perfluorocyclobutane are then discharged from the reactor.

After each time that perfluorocyclobutane has been discharged, the liquid mixture remaining in the reactor is re-heated to a temperature between 160° and 235° C. The reactor is charged with a molar excess of TFE so as to result in a total reactor pressure between 1.7 and 3.4 MPa (preferably 2.1 to 3.1 MPa, most preferably 2.6 to 2.9 MPa) and the telomerization reaction allowed to proceed.

Optionally, the process of this invention may begin with the reaction of iodine and TFE to form 1,2-diiodoperfluoroethane, which then thermally decomposes to form the I—$(CF_2CF_2)$·radical and the process proceeds as above.

EXAMPLES

Comparative Example A

A one-liter reactor was charged with iodine (500 grams) and tetrafluoroethylene (TFE, 80 grams). The reactor was heated to 130° C. and additional TFE (120 grams) was added to the reactor at a rate of 1 gram/min. After the addition was completed, the reactor was heated to 225° C. Another portion of TFE (300 grams) was then added at the rate of 1 gram/min. After TFE addition was complete, the reaction was allowed to proceed for 12 hours at 245° C. During most of the reaction period, pressure was in the 3.65–3.86 MPa range. After cooling and discharging, the product mixture obtained weighed 550 grams. Gas chromatography analysis indicated that this product had a composition C2:C4:C6:C8:C10=7.29:48.27:29.68:10.50:3.64 (mole %), wherein the abbreviations C2, C4, C6, C8, and C10 stand for 1,2-diiodoperfluoroethane; 1,4-diiodoperfluorobutane; 1,6-diiodoperfluorohexane; 1,8-diiodoperfluorooctane; and 1,10-diiodoperfluorodecane, respectively.

Comparative Example B

A one-gallon autoclave was charged with iodine (1700 grams) and tetrafluoroethylene (TFE, 272 grams). The reactor was heated to 130° C. and additional TFE (408 grams) was added to the reactor at a rate of 4 grams/min. After TFE addition was completed, the reactor was heated to 225° C. Another portion of TFE (1020 grams) was then added at the rate of 4 grams/min. After TFE addition was completed, the reaction was allowed to proceed for 10 hours at 245° C. During most of the reaction period, the reactor pressure was in the 3.72–4.14 MPa range. After cooling and discharging, the product mixture obtained weighed 1924 grams (average of 7 runs). Gas chromatography analysis indicated that the product had an average composition C2:C4:C6:C8:C10= 7.08:49.52:29.91:10.73:2.77 (mole %)

Comparative Examples A and B indicate that a high reaction temperature and high pressure were required to achieve reasonable I—$(CF_2CF_2)_n$—I ($n \geq 2$) oligomer formation. Yet the total product recovery was relatively low (55–57%).

Comparative Example C

A one-gallon reactor was charged with 1,2-diiodoperfluoroethane (1700 grams). The reactor was sealed and cool-evacuated, and then tetrafluoroethylene (TFE) was fed to the reactor until the total pressure in the reactor reached about 0.41 MPa. The reactor was heated to 220° C. and additional TFE was added to maintain the total reactor pressure at 1.72 MPa. The reaction was allowed to proceed for 20 hours under these conditions. A total of 676 grams of TFE was fed to the reactor. After cooling and discharging, the product mixture obtained weighed 1378 grams. Gas chromatography analysis indicated that this product had a composition C2:C4:C6:C8=66.18:28.02:3.26:0.17 (mole %).

Comparative Example D

A one-liter reactor was charged with 1,2-diiodoperfluoroethane (977 grams). The reactor was sealed and cool-evacuated and then heated to 215° C. Tetrafluoroethylene (TFE) was transferred into the reactor until the total pressure in the reactor reached 3.03 MPa. The reaction was allowed to proceed for 20 hours under these conditions. Then the reactor contents were cooled to 160° C. and additional tetrafluoroethylene was fed so as to result in a reactor pressure 0.69 MPa over the observed pressure. The reaction proceeded for 5 hours before it was quenched by cooling. A total of 230 grams of TFE was fed to the reactor. The product mixture obtained weighed 1063 grams. Gas chromatography analysis indicated that this product has a composition C2:C4:C6:C8=61.14:29.18:5.67:0.70 (mole %).

Comparative Example E

A one-liter reactor was charged with 1,2-diiodoperfluoroethane (977 grams). The reactor was sealed, cool-evacuated and then heated to 215° C. Tetrafluoroethylene (TFE) was then fed to the reactor until the total pressure in the reactor reached 3.1 MPa. The reaction was allowed to proceed for 20 hours under these conditions. Then the reactor contents were cooled to 160° C. and additional tetrafluoroethylene was fed so as to result in a reactor pressure 0.34 MPa over the observed pressure. The reaction proceeded for another 6 hours before quenching by cooling. A total of 158 grams of TFE was fed to the reactor. The product mixture obtained weighed 1081 grams. Gas chromatography analysis indicated that this product has a composition C2:C4:C6:C8=53.38:34.17:8.41:1.32 (mole %).

Comparative Examples C–E indicate that conversions to the high oligomer I—$(CF_2CF_2)_n$—I ($n \geq 2$) were quite low when reaction temperatures and reaction pressures similar to those employed in the process of this invention were employed, but without periodically discharging the perfluorocyclobutane byproduct from the reactor.

Example 1

A one-liter autoclave was charged with 1,2-diiodoperfluoroethane (977 grams). The reactor was heated to 225° C., and tetrafluoroethylene (TFE) was added until the total pressure in the reactor reached 2.76 MPa. The reaction was allowed to proceed for 10 hours. Then, reactor contents were cooled to 50° C., and the overhead gas was discharged. The reactor was re-heated to 225° C., and tetrafluoroethylene (TFE) was again fed to the reactor until the total pressure in the reactor reached 2.76 MPa. The reaction was allowed to proceed for another 10 hours. The reactor contents were then cooled to 50° C. and the overhead gas was again discharged. Then the reactor was re-heated to 160° C. and additional tetrafluoroethylene was fed until the pressure was 0.69 MPa over the observed pressure. The reaction proceeded for an additional 2.5 hours. A total of 773 grams of TFE was fed to the reactor. The product mixture obtained weighed 1220 grams. Gas chromatography (GC) analysis indicated that this product had a composition C2:C4:C6:C8:C10=28.83:38.67:21.89:8.31:2.31 (mole %).

Example 2

A one-liter reactor was charged with 1,2-diiodoperfluoroethane (977 grams). The reactor was heated to 225° C., and tetrafluoroethylene (TFE) was added until the total reactor pressure reached 2.76 MPa. The reaction was allowed to proceed for 6 hours. The reactor contents were then cooled to 50° C. and the overhead gas was discharged. Then the reactor was re-heated to 225° C., and tetrafluoroethylene (TFE) was again fed to the reactor until the total pressure in the reactor reached 2.76 MPa. The reaction was allowed to proceed for another 6 hours. The reactor contents were then cooled to 50° C. and the overhead gas was again discharged. The reactor was then re-heated to 160° C., and additional tetrafluoroethylene was fed so as to result in a pressure of 0.69 MPa over the observed pressure. The reaction proceeded for an additional hour. A total of 609 grams of TFE was fed to the reactor. The product mixture obtained weighed 1185 grams. Gas chromatography analysis indicated that this product had a composition C2:C4:C6:C8:C10=33.05:40.38:19.08:6.06:1.42 (mole %).

Example 3

A one-liter reactor was charged with 1,2-diiodoperfluoroethane (545 grams) and iodine (526 grams). The reactor was heated to 160° C. Tetrafluoroethylene (TFE) was then fed to the reactor so as to result in a pressure 0.69 MPa over the observed pressure at this temperature. The reaction was allowed to proceed for 3 hours. Reactor contents were then cooled to 50° C. and the overhead gas was discharged. The reactor was then re-heated to 225° C., and tetrafluoroethylene (TFE) was again added to the reactor until the total reactor pressure reached 2.76 MPa. The reaction was allowed to proceed for another 6 hours. Reactor contents were then cooled to 50° C. and the overhead gas was again discharged. The reactor was then reheated to 225°

C., and TFE was again fed to the reactor until the total pressure in the reactor reached 2.76 MPa. The reaction was allowed to proceed for another 6 hours. Reactor contents were then cooled to 50° C. and the overhead gas was again discharged. The reactor was then re-heated to 160° C., and additional TFE was fed to so as to result in a reactor pressure of 0.69 MPa over the observed pressure. The reaction proceeded for an additional hour. A total of 1011 grams of TFE was fed to the reactor. The product mixture obtained weighed 1388 grams. Gas chromatography analysis indicated that this product had a composition C2:C4:C6:C8:C10=38.62:41.14:15.60:3.94:0.70 (mole %).

The results from Examples 1–3 clearly indicate that periodically discharging the overhead gas in the reactor greatly increases the conversion to the high oligomer I—$(CF_2CF_2)_n$—I (n≧2). Less than 40 mole % of C2 was found in the final product mixtures when the process of this invention was employed.

What is claimed is:

1. A process for preparing α, ω-diiodoperfluoroalkanes comprising the steps of:
    A. heating 1,2-diiodoperfluoroethane in a reactor to a temperature between 200° and 240° C.;
    B. adding to said reactor a quantity of tetrafluoroethylene so as to result in a total pressure in said reactor of between 1.7 and 3.4 MPa;
    C. maintaining said temperature and pressure for a period of time to form a mixture of α, ω-diiodoperfluoroalkanes and perfluorocyclobutane;
    D. cooling said mixture to a temperature below 75° C. and then discharging gaseous perfluorocyclobutane and unreacted tetrafluoroethylene from said reactor, leaving a liquid mixture in said reactor;
    E. heating said liquid mixture to a temperature between 160° and 235° C.; and
    F. repeating steps B)–E) until a desired mixture has been prepared of α, ω-diiodoperfluoroalkanes of the formula I—$(CF_2CF_2)_n$—I, wherein n is an integer from 2 to 6.

2. A process according to claim 1 wherein said 1,2-diiodoperfluoroethane is made by the reaction of iodine with tetrafluoroethylene at a temperature between 100° and 235° C.

3. A process according to claim 1 wherein step A) is performed at a temperature between 210° and 235° C.

4. A process according to claim 3 wherein step A) is performed at a temperature between 220° and 230° C.

5. A process according to claim 1 wherein step B) is performed at a total pressure between 2.1 and 3.1 MPa.

6. A process according to claim 5 wherein step B) is performed at a total pressure between 2.6 and 2.9 MPa.

7. A process according to claim 1 wherein said mixture of α, ω-diiodoperfluoroalkanes in step F) consists essentially of α, ω-diiodoperfluoroalkanes having n values from 2 to 4.

8. A process according to claim 7 wherein said mixture of α, ω-diiodoperfluoroalkanes in step F) consists essentially of α, ω-diiodoperfluoroalkanes having n values from 2 to 3.

* * * * *